US011419881B2

(12) United States Patent
Monti

(10) Patent No.: US 11,419,881 B2
(45) Date of Patent: Aug. 23, 2022

(54) TREATMENT OF MIGRAINE

(71) Applicant: Pherin Pharmaceuticals, Inc., Mountain View, CA (US)

(72) Inventor: Louis Monti, Mountain View, CA (US)

(73) Assignee: Pherin Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 16/841,937

(22) Filed: Apr. 7, 2020

(65) Prior Publication Data

US 2020/0323884 A1    Oct. 15, 2020

Related U.S. Application Data

(60) Provisional application No. 62/833,994, filed on Apr. 15, 2019.

(51) Int. Cl.
*A61K 31/58* (2006.01)
*A61K 9/00* (2006.01)

(52) U.S. Cl.
CPC ............ *A61K 31/58* (2013.01); *A61K 9/0034* (2013.01); *A61K 9/0043* (2013.01)

(58) Field of Classification Search
CPC .... A61K 9/0043; A61K 9/0034; A61K 31/58; A61P 29/00
See application file for complete search history.

(56) References Cited

U.S. PATENT DOCUMENTS

| | | | |
|---|---|---|---|
| 5,303,703 A | 4/1994 | Monti-Bloch | |
| 6,057,439 A | 5/2000 | Jennings-White et al. | |
| 6,331,534 B1 | 12/2001 | Berliner et al. | |
| 8,431,559 B2 | 4/2013 | Monti | |
| 2012/0108558 A1* | 5/2012 | Monti | A61P 17/00 514/172 |
| 2013/0138167 A1* | 5/2013 | Bradley | A61N 1/36139 607/5 |
| 2013/0158450 A1* | 6/2013 | Juto | G16H 20/70 601/46 |

FOREIGN PATENT DOCUMENTS

| EP | 0914165 B1 * | 10/2006 | ............. A61P 15/00 |
|---|---|---|---|
| WO | 2009/126825 A1 | 10/2009 | |

OTHER PUBLICATIONS

Rozen, T.D.; title: Migraine headache: Immunosuppressant therapy; Curr Treat Options Neurol; vol. 4, pp. 395-401, Sep. 2002. (Year: 2002).*
Unknown author; title: The Timeline of a Migraine Attack, Published by American Migraine Foundation on Jan. 18, 2018. (Year: 2018).*
Woldeamanuel et al; title: What Is the Evidence for the Use of Corticosteroids in Migraine? Curr Pain Headache Rep; vol. 18, p. 464 ; published Nov. 6, 2014. (Year: 2014).*
Fiesseler et al, title: Steroids for migraine headaches: a randomized double-blind, two-armed, placebo-controlled trial, J Emerg Med. Apr. 2011; vol. 40, No. 4; pp. 463-468 (Year: 2011).*
Lords et al, title: Traumatic Migraine Versus Concussion: A Case Report, Sep.-Oct. 2014 issue; published J20184(Year: 2014).*
Marmura,MJ, et al., "The Acute Treatment of Migraine in Adults: The American Headache Society Evidence Assessment of Migraine Pharmacotherapies", Headache, vol. 55(1), pp. 3-20 (2015).
American Academy of Neurology, "Practice Guideline Update Summary: Botulinum neurotoxin for the treatment of blepharospasm, cervical dystonia, adult spasticity, and headache", Neurology, vol. 86(19), pp. 1818-1826 (2016).
American Headache Society, "AHS Consensus Statement: The American Headache Society Position Statement on Integrating New Migraine Treatments Into Clinical Practice", Headache, vol. 59(1), pp. 1-18 (2019).
Burstein, R, et al., "Migraine: Multiple Processes, Complex Pathophysiology", J. Neuroscience, vol. 35(17), pp. 6619-6629 (2015).
Chen, Z, et al., "Altered functional connectivity of amygdala underlying the neuromechanism of migraine pathogenesis", J. Headache Pain, vol. 18(7), DOI 10.1186/s10194-017-0722-5 (2017).
clinicaltrials.gov, NCT01217775 "Intranasal PH80 Spray for Acute Management of the Symptoms of Premenstrual Dysphoric Disorder (PH80-PMD)".
Denuelle, M, et al., "Hypothalamic Activation in Spontaneous Migraine Attacks", Headache, vol. 47(1), pp. 1418-1426(2007).
Freeman, EW, et al., "Evaluation of a Unique New Low-Dose Intranasal Aerosol in the Treatment of Clinically Significant Premenstrual Syndrome", Abstract from a presentation at the New Clinical Drug Evaluation Unit Annual Meeting, 2007.
Grosser, BI, et al., "Behavioral and electrophysiological effects of androstadienone, a human pheromone", Psychoneuroendocrinology, vol. 25, pp. 289-299 (2000).
Kahriman, A, et al., "Migraine and Tension-Type Headache", Semin. Neurol., vol. 38(6), pp. 608-618 (2018).
Lee, MJ, et al., "Increased connectivity of pain matrix in chronic migraine: a resting-state functional MRI study", J. Headache Pain, vol. 20(29), DOI 10.1186/s10194-019-0986-z (2019).
May, A, et al., "Hypothalamic regulation of headache and migraine", Cephalalgia, vol. 39(13), pp. 1710-1719 (2019) [First published online Aug. 29, 2019].
Monti-Bloch, L, et al., "Effect of putative pheromones on the electrical activity of the human vomeronasal organ and olfactory epithelium", J. Steroid Biochem. Mol. Biol., vol. 39(4), pp. 573-582 (1991).
Monti-Bloch, L, et al., "The Human Vomeronasal System: A Review", Ann. N.Y. Acad. Sci., vol. 855, pp. 373-389 (1998).
Silberstein, SD et al., "Evidence-based guideline update: Pharmacologic treatment for episodic migraine prevention in adults", Neurology, vol. 78(17), pp. 1337-1345 (2012).

(Continued)

*Primary Examiner* — Ali Soroush
(74) *Attorney, Agent, or Firm* — HDC IP Law, LLP; Sam L. Nguyen

(57) ABSTRACT

16α,17α-Epoxy-10β-hydroxyestr-4-en-3-one is useful in the treatment of migraine by nasal administration.

20 Claims, No Drawings

(56) References Cited

OTHER PUBLICATIONS

Stensaas, LJ, et al., "Ultrastructure of the human vomeronasal organ", J. Steroid Biochem. Mol. Biol., vol. 39(4), pp. 553-560 (1991).
Kuhl, "Pharmacology of estrogens and progestagens: influence of different routes of administration", Climacteric, vol. 8(Suppl. 1), pp. 3-63 (2005).
Wikipedia, "Estradiol"; URL: https://en.wikipedia.org/wiki/Estradiol, retrieved Mar. 24, 2021.
Monti-Bloch et al., "The Human Vomeronasal System", Psychoneuroendocrinology, 19, 673-686 (1994).

* cited by examiner

TREATMENT OF MIGRAINE

CROSS-REFERENCE TO RELATED APPLICATION

This application claims the benefit under 35 USC 119(e) of Application No. 62/833,994, "Treatment of migraine", filed 15 Apr. 2019, the entire content of which is incorporated into this application by reference.

FIELD OF THE INVENTION

This invention relates to the treatment of migraine.

DESCRIPTION OF THE RELATED ART

Migraine

According to Burstein et al., "Migraine: Multiple Processes, Complex Pathophysiology", *J. Neuroscience*, vol. 35(17), pp. 6619-6629 (2015), migraine is a recurrent headache disorder affecting about 15% of the population during the formative and most productive periods of their lives, between the ages of 22 and 55. It frequently starts in childhood, particularly around puberty, and affects women more than men (3:1 female-to-male ratio). It tends to run in families and, as such, is considered a genetic disorder. According to the Merck Manual, Professional Version, online, https://www.merckmanuals.com/professional/neurologic-disorders/headache/migraine, evidence based on evaluation of veterans of the Iraq and Afghanistan conflicts suggests that migraine may frequently develop after mild traumatic brain injury.

In some cases, the migraine headache begins with no warning signs and ends with sleep. In other cases, the migraine headache may be preceded by a premonitory or prodromal phase that may begin as much as 3 days before the start of the migraine headache, allowing patients to predict the onset of a migraine headache well before its onset. Common premonitory symptoms involve the hypothalamus, brainstem, limbic system, and certain cortical areas, and include fatigue; euphoria; depression; irritability/anger; food cravings; constipation; neck stiffness; increased yawning; and/or abnormal sensitivity to light, sound, and smell. The migraine headache may also be preceded by an aura phase (seen in about 25% of migraine patients) that includes a variety of focal cortically mediated neurological symptoms that appear just before and/or during the headache phase. Symptoms of migraine aura develop gradually, feature excitatory and inhibitory phases, and resolve completely. Positive (gain-of-function) and negative (loss-of-function) symptoms may present as scintillating lights and scotomas when affecting the visual cortex; paresthesia, and numbness of the face and hands when affecting the somatosensory cortex; tremor and unilateral muscle weakness when affecting the motor cortex or basal ganglia; and difficulty saying words (aphasia) when affecting the speech area.

The migraine headache is commonly unilateral, pulsating, aggravated by routine physical activity, and can last a few hours to a few days. As the migraine headache progresses, it may be accompanied by a variety of autonomic symptoms (nausea, vomiting, nasal/sinus congestion, rhinorrhea, lacrimation, ptosis, yawning, frequent urination, and diarrhea), affective symptoms (depression and irritability), cognitive symptoms (attention deficit, difficulty finding words, transient amnesia, and reduced ability to navigate in familiar environments), and sensory symptoms (photophobia, phonophobia, osmophobia, muscle tenderness, and cutaneous allodynia).

Fluctuating estrogen levels are a potent migraine trigger. Many women have onset of migraine at menarche, severe attacks during menstruation (menstrual migraine), and attacks worsening during menopause. For most women, migraines remit during pregnancy, but sometimes they worsen during the first or second trimester; often they worsen after childbirth, when estrogen levels decrease rapidly. Oral contraceptives and other hormone therapy occasionally trigger or worsen migraine and have been associated with stroke in women who have migraine with aura.

Patients with episodic migraine (EM), headaches on no more than fourteen days per month, can develop chronic migraine. Chronic migraine (CM) is diagnosed in patients who, on average, have at least fifteen days of headache a month, with the headaches on at least eight of those days having features of migraine, for at least three months. This headache disorder used to be called combination or mixed headache because it had features of both migraine and tension-type headache. These CM headaches often develop in patients who overuse drugs for acute treatment of EM headaches.

Based on current knowledge, the brain regions related to pain processing and modulation include the prefrontal cortex, cingulate cortex, insular cortex, thalamus, basal ganglia, cerebellum and periaqueductal grey matter. Recent high-resolution magnetic resonance imaging (MRI) studies report activation and increased functional connectivity of the hypothalamus and the amygdala in very early stages of the migraine episodes and propose the hypothalamus as the site of generation of the migraine attacks. Denuelle et al., "Hypothalamic Activation in Spontaneous Migraine Attacks", *Headache*, vol. 47(1), pp. 1418-1426 (2007), report a positron imaging tomography (PET) study using $H_2^{15}O$ in seven migraine sufferers, scanned during a spontaneous migraine attack, after relief of the headache with sumatriptan, and during an attack-free interval 15-60 days after the measured attack; and saw significant activation in the midbrain, pons, and hypothalamus during the headache, all persisting after headache relief. Chen et al., "Altered functional connectivity of amygdala underlying the neuro-mechanism of migraine pathogenesis", *J. Headache Pain*, vol. 18(7), DOI 10.1186/s10194-017-0722-5 (2017), report MRI studies, including functional magnetic resonance imaging (fMRI) in normal controls (NC) and sufferers with both EM and CM; and saw increased functional connectivity of the left amygdala in EM and decreased functional connectivity of the right amygdala in CM relative to NC, and increased functional connectivity of bilateral amygdala in CM relative to EM. They concluded that the altered functional connectivity of the amygdala demonstrated that neurolimbic pain network contributes to the pathogenesis of EM and the chronification of CM. Lee et al., "Increased connectivity of pain matrix in chronic migraine: a resting-state functional MRI study", *J. Headache Pain*, vol. 20(29), DOI 10.1186/s10194-019-0986-z (2019), report an fMRI study of EM and CM sufferers; and conclude that CM sufferers have a stronger functional connectivity in the pain matrix than do EM sufferers, that the pain matrix is functionally correlated with the hypothalamus and dorsal raphe nucleus, and that functional alteration of the pain matrix may play a role in migraine chronification. May et al., "Hypothalamic regulation of headache and migraine", *Cephalalgia*, vol. 39(13), pp. 1710-1719 (2019), discuss recent work in the field, and "review clinical and neuroscience evidence that puts the hypothalamus in the center of scientific attention when attack generation is discussed."

For some patients, migraine is an infrequent, tolerable inconvenience. For others, it is a devastating disorder resulting in frequent periods of incapacity, loss of productivity, and severely impaired quality of life.

The Pharmacological Treatment of Migraine

Migraine treatment can include preventive therapy aimed at reducing the frequency and/or severity of migraine attacks (i.e. inhibiting the occurrence of migraine, or of one or more of its symptoms, or causing the migraines or symptoms to be less severe when a migraine attack occurs), and acute therapy used to abort a migraine attack (inhibit the migraine or its symptoms, and relieve or palliate the migraine or its symptoms, when a migraine attack occurs).

According to Kahriman et al., "Migraine and Tension-Type Headache", *Semin. Neurol.*, vol. 38(6), pp. 608-618 (2018), acute treatments for migraine can be can be separated into three main classes: (1) the nonspecific analgesics (e.g., acetaminophen), (2) migraine-specific analgesics (e.g., triptans and ergots), and (3) adjunctive treatment for other associated symptoms (e.g., antiemetics).

The American Headache Society considers acetaminophen, ibuprofen, naproxen, and diclofenac "established as effective for acute migraine treatment" with ketorolac "probably effective"; and considers the antiemetics metoclopramide and prochlorperazine "probably effective". It considers the triptans and ergots "established as effective", though triptans have largely replaced ergots because of the more problematic side effect profile and lower convenience of ergots; but the triptans can also cause vasoconstriction and are contraindicated in those with vascular disease such as coronary artery disease, ischemic stroke, peripheral arterial disease, and Raynaud's disease. Finally, it considers butalbital and opioids "possibly effective", though they are not recommended for routine use because of the risk of dependence and abuse.

According to the "Evidence-based guideline update: Pharmacologic treatment for episodic migraine prevention in adults", *Neurology*, vol. 78(17), pp. 1337-1345 (2012), the American Academy of Neurology and American Headache Society consider the antiepileptics divalproex sodium, sodium valproate, and topiramate to have "established efficacy" as migraine preventive therapy, but the valproates can cause a number of side effects including alopecia, GI upset, hepatic dysfunction, thrombocytopenia, tremor, and weight gain, and they are contradicted in pregnant women because of the risk of teratogenicity, while topiramate can cause weight loss and CNS adverse effects. The β-blockers metoprolol, propranolol, and timolol are also considered to have "established efficacy", but only β-blockers without intrinsic sympathomimetic activity should be used, and all should be avoided in patients with bradycardia, hypotension, diabetes, or asthma. Other β-blockers atenolol and nadolol are considered "probably effective". The antidepressants amitriptyline and venlafaxine are also considered "probably effective", but amitriptyline has anticholinergic effects and causes weight gain. Many other drugs of the same and different classes have also been tested, but were considered either "possibly effective", lacked adequate data, or were even "established as not effective" (lamotrigine), "probably not effective" (clomipramine), or "possibly not effective" (several compounds).

Onabotulinumtoxin A (Allergan's BOTOX®) has been approved by the US FDA for the treatment of chronic migraine. A single treatment consists of injections of 0.1 mL (5 units) of onabotulinumtoxin A at 31 different sites in the superficial sites of seven different head and neck muscle areas. An initial course of treatment involves two treatments twelve weeks apart, and retreatment every twelve weeks is recommended. According to the American Academy of Neurology practice guideline, "Botulinum neurotoxin for the treatment of blepharospasm, cervical dystonia, adult spasticity, and headache", *Neurology*, vol. 86(19), pp. 1818-1826 (2016), onabotulinumtoxin A "should be offered as a treatment option to patients with chronic migraine to increase the number of headache-free days" and "should be considered to reduce headache impact on health-related quality of life", but should not be offered as a treatment for episodic migraine.

As discussed in "AHS Consensus Statement: The American Headache Society Position Statement on Integrating New Migraine Treatments Into Clinical Practice", *Headache*, vol. 59(1), pp. 1-18 (2019), emerging preventive options include humanized monoclonal antibodies against calcitonin gene-related peptide (CGRP), with three agents approved by the US FDA: erenumab (targeting the CGRP receptor), and fremanezumab and galcanezumab (targeting the CGRP ligand). All three agents are administered by subcutaneous injection every four weeks, and fremanezumab may also be administered by subcutaneous injection quarterly, using three administrations of the four-weekly dose.

Notwithstanding the present agents, there still exists a need for effective and tolerable therapy for migraine.

Nasal Chemosensory Receptors and Pherines

In most species, including humans, neuroepithelial cells in the mucosal lining of the dorsal nasal recess and the nasal septum, including the vomeronasal organ ("VNO", a bilateral chemosensory organ found in most vertebrates including humans) have chemosensory receptors associated with odor and pheromone detection (see generally Muller-Schwarze and Silverstein, "Chemical Signals", Plenum Press, New York (1980); Monti-Bloch et al., "Effect of putative pheromones on the electrical activity of the human vomeronasal organ and olfactory epithelium", *J. Steroid Biochem. Mol. Biol.*, vol. 39(4), pp. 573-582 (1991); Monti-Bloch et al., "The Human Vomeronasal System: A Review", *Ann. N.Y. Acad. Sci.*, vol. 855, pp. 373-389 (1998)). The axons of the neuroepithelial cells of the nasal chemosensory receptors, including the VNO, have direct oligosynaptic input to the hypothalamus and limbic amygdala of the brain, while the distal processes (microvilli) have chemosensory receptors (Stensaas et al., "Ultrastructure of the human vomeronasal organ", *J. Steroid Biochem. Mol. Biol.*, vol. 39(4), pp. 553-560 (1991)).

Human putative pheromones delivered to the nasal septal area bind to local chemosensory receptors and trigger nerve signals that reach the brain inducing physiological and behavioral changes (Grosser et al., "Behavioral and electrophysiological effects of androstadienone, a human pheromone", *Psychoneuroendocrinology*, vol. 25, pp. 289-299 (2000)). Synthetic analogs of human pheromones called pherines (odorless substances that bind to nasal chemosensory receptors, including receptors in the VNO) can induce robust physiological, pharmacological and behavioral effects when delivered airborne to these receptors via the nasal passages. This information is supported by several studies in human volunteers using fMRI and PET, showing that pherines selectively activate the brain areas (hypothalamus, limbic system, cingulate gyrus, anterior thalamus and prefrontal cortex) where their physiological, pharmacological and behavioral effects are integrated. Studies with several pherines have shown that, because the compounds act directly on nasal chemosensory receptors which are connected to the brain by short neural circuits, administration of the compounds causes an effect on physiological markers (e.g. autonomic nervous system responses and EEG) within seconds to less than a minute, and an effect on behavior and on endocrine and neurotransmitter metabolite markers within about 10-15 minutes.

16α,17α-Epoxy-10β-hydroxyestr-4-en-3-one

U.S. Pat. No. 6,057,439, "Steroids as neurochemical stimulators of the VNO to alleviate symptoms of PMS and anxiety", describes the use of a number of steroidal pherines for the treatment of premenstrual dysphoric disorder ("PMDD", also referred to as "premenstrual syndrome" or "PMS"). and anxiety by administration to the vomeronasal organ of an individual suffering from those symptoms. 16α,17α-Epoxy-10β-hydroxyestr-4-en-3-one is described in the patent, where it is referred to as 16α,17α-epoxyestr-4-en-10β-ol-3-one. The patent discloses the synthesis of the compound, and claims the compound and pharmaceutical compositions containing it for alleviating the symptoms of PMDD. U.S. Pat. No. 6,331,534, "Steroids as neurochemical stimulators of the VNO to alleviate pain", describes the same steroids for alleviating pain by vomeronasal administration. U.S. Pat. No. 8,431,559, "Treatment of hot flashes", describes a synthesis of 16α,17α-epoxy-10β-hydroxyestr-4-en-3-one, and the use of 16α,17α-epoxy-10β-hydroxyestr-4-en-3-one for alleviating hot flashes by vomeronasal administration.

The disclosures of the documents referred to in this application are incorporated into this application by reference.

SUMMARY OF THE INVENTION

In a first aspect, this invention is a method for the treatment of migraine (treatment of individuals suffering from migraine) by nasal administration of 16α,17α-epoxy-10β-hydroxyestr-4-en-3-one.

In another aspect, this invention thus includes pharmaceutical formulations and devices containing 16α,17α-epoxy-10β-hydroxyestr-4-en-3-one for the treatment of migraine by nasal administration.

16α,17α-Epoxy-10β-hydroxyestr-4-en-3-one has particular utility in the treatment of migraine (treatment of individuals suffering from migraine); and is expected to have the following advantages over conventional treatments:

(1) ease of administration while retaining the ability for acute use;

(2) rapid onset of effect, because of the direct local delivery of the compound to nasal chemosensory receptors and consequent action. Current oral antimigraine agents, like other oral agents in general, may take 30 minutes or more for therapeutic effectiveness to be achieved; and (3) lack of local nasal adverse effects and lack of systemic effects or toxicity, because of the local route of administration, the effect on peripheral (nasal) chemosensory receptors and the demonstrated lack of systemic bioavailability, and the effect on the central nervous system through the activation of short (oligosynaptic) neural circuits.

Preferred embodiments of this invention are characterized by the specification and by the features of claims 1 to 20 of this application as filed.

DETAILED DESCRIPTION OF THE INVENTION

Definitions

Migraine and its treatment are described in the subsections entitled "Migraine" and "The pharmacological treatment of migraine" of the DESCRIPTION OF THE RELATED ART.

"Comprising" or "containing" and their grammatical variants are words of inclusion and not of limitation and mean to specify the presence of stated components, groups, steps, and the like but not to exclude the presence or addition of other components, groups, steps, and the like. Thus "comprising" does not mean "consisting of", "consisting substantially of", or "consisting only of"; and, for example, a formulation "comprising" a compound must contain that compound but also may contain other active ingredients and/or excipients.

"Nasal administration" is administration to human nasal chemosensory receptors, including the receptors of the VNO. In a clinical setting, this may be accomplished by the use of a probe specifically designed to administer the 16α,17α-epoxy-10β-hydroxyestr-4-en-3-one essentially solely to the VNO (such a probe, also designed to measure the effect on vomeronasal tissue, is described in Monti-Bloch, U.S. Pat. No. 5,303,703, "Combined neuroepithelial sample delivery electrode device and methods of using same"). More usually, however, nasal administration comprises administration to the nasal passages in a manner that desirably directs the 16α,17α-epoxy-10β-hydroxyestr-4-en-3-one generally towards the nasal chemosensory receptors, including the receptors of the VNO, such as by use of conventional nasal spray technology customarily used for nasal delivery of steroids for allergies and asthma.

A "therapeutically effective amount" means the amount of 16α,17α-epoxy-10β-hydroxyestr-4-en-3-one that, when administered to the nasal chemosensory receptors of an individual suffering from migraine, is sufficient to effect treatment for the migraine, but which amount is insufficient to have a systemic effect on the migraine by absorption into the circulation. "Treating" or "treatment" of migraine disorder includes one or more of:

(1) inhibiting the occurrence of migraine, or of a symptom thereof;

(2) relieving migraine, or a symptom thereof, when it occurs, and (3) palliating the symptoms of migraine.

16α,17α-Epoxy-10β-hydroxyestr-4-en-3-one and its Preparation

The preparation of 16α,17α-epoxy-10β-hydroxyestr-4-en-3-one is described in U.S. Pat. No. 6,057,439; and a preparation from the readily commercially available steroid estrone, 3-hydroxy-estra-1,3,5(10)-trien-17-one, is described in U.S. Pat. No. 8,431,559.

A person of ordinary skill in the art will have no difficulty, considering that skill and U.S. Pat. Nos. 6,057,439 and 8,431,559, in preparing 16α,17α-epoxy-10β-hydroxyestr-4-en-3-one.

Formulation and Administration

The 16α,17α-epoxy-10β-hydroxyestr-4-en-3-one may be administered nasally by any suitable route. Routes of administration include, but are not limited to, topical applications (e.g. of an nasal cream or gel), nasal spray, nasal powder spray, aerosol, and the like. Pharmaceutical formulations generally will be formulations designed to administer the drug across mucosal membranes. Suitable formulations for each of these methods of administration may be found, for example, in Gennaro, ed., "Remington: The Science and Practice of Pharmacy", 20 ed., Lippincott Williams & Wilkins, Philadelphia, Pa., (2003). Typical preferred formulations will be aqueous solutions for nasal spray, and will contain 16α,17α-epoxy-10β-hydroxyestr-4-en-3-one and water, typically will also contain one or more other pharmaceutically acceptable excipients to increase the aqueous solubility of the 16α,17α-epoxy-100-hydroxyestr-4-en-3-one, such as alcohols and glycols (for example, ethanol and propylene glycol) and surfactants (for example, polysorbate 80 (polyoxyethylene (20) sorbitan monooleate)), and may also contain one or more other pharmaceutically acceptable excipients such as buffers, preservatives (antioxidants, chelating agents, etc.), tonicifiers, viscosity enhancers (dextrans, cyclodextrins, polyvinylpyrrolidones, polyethylene glycols, etc.), and the like, such as are well-known for aqueous solutions for nasal spray. Suitable delivery devices for these formulations are the metered-dose nasal spray pumps in common use for nasal delivery of steroids for allergies and asthma. Such pumps are made by a number of manufacturers, for example Aptar. Liquid volumes should be such that the formulation is efficiently delivered without exceeding the nasal retention volume with an excess either flowing back into the nasal sinuses or dripping from the nose, and a volume of 100 μL has been found convenient, though greater or lesser volumes (50 μL has been satisfactorily tested) will also be satisfactory. Desirably, the aqueous solution formulations and the delivery devices used to administer them will be chosen to achieve maximum retention of the sprayed formulation within the nasal passages, for example by choosing them such that the mean size of the sprayed droplets will be between about 30 and 50 microns. For powder formulations, a particle size between about 50 and 100 microns is generally considered suitable.

Exemplary aqueous solution formulations include the two formulations discussed in Example 4 below. A further exemplary formulation is as follows:

| Component | Quantity | Grade |
|---|---|---|
| 16α,17α-epoxy-10β-hydroxyestr-4-en-3-one | 16 μg/mL | GMP |
| ethanol | 2% v/v | USP |
| propylene glycol | 3% v/v | USP |
| polysorbate 80 | 0.5% w/v | USP |
| benzalkonium chloride 50% | 0.001% v/v | USP |
| sterile Water For Injection (WFI) | to 100% | USP. |

A person of ordinary skill in the art will have no difficulty, considering that skill and this disclosure, in preparing suitable formulations and delivery systems of 16α,17α-epoxy-10β-hydroxyestr-4-en-3-one for nasal administration.

A therapeutically effective amount of 16α,17α-epoxy-100-hydroxyestr-4-en-3-one, when administered in an nasal spray formulation of the type above, is about 0.8 to 19.2 μg per administration, preferably 1.6 to 9.6 μg per administration, for example about 1.6 μg, 3.2 μg, or 6.4 μg per administration. For a 16 mg/L (16 ppm) concentration of 16α,17α-epoxy-10β-hydroxyestr-4-en-3-one in the formulation, each administration of 1.6 μg would therefore be 100 μL of the formulation, conveniently a single administrations of 100 μL to one nostril, each administration of 3.2 μg would be 200 μL of the formulation, conveniently a single administration of 100 μL to each nostril; and each administration of 6.4 μg would be 400 μL of the formulation, conveniently two administrations of 100 μL to each nostril. It is expected that not more than a few percent of this dose will actually reach the nasal chemosensory receptors and the VNO, so therapeutically effective amounts when administered essentially solely to the nasal chemosensory receptors will be perhaps 20-fold lower. A person of ordinary skill in the art will have no difficulty, considering that skill and this disclosure, in determining a therapeutically effective amount of 16α,17α-epoxy-10β-hydroxyestr-4-en-3-one for other formulations. These doses, both nasal and direct vomeronasal/ to the nasal chemosensory receptors, are well below any level that would cause a systemic effect other than those effects mediated through the nasal chemosensory receptors including receptors of the VNO.

Initial pharmacological response to the nasal administration of 16α,17α-epoxy-10β-hydroxyestr-4-en-3-one takes place very rapidly, typically within seconds to a minute after administration. More complete pharmacological response occurs slightly more slowly; but an effect on migraine (or on one or more symptoms of migraine) is expected within 5 to 15 minutes. Because of the rapid onset of effect and safety of nasally administered 16α,17α-epoxy-10β-hydroxyestr-4-en-3-one, it is expected that the compound may be administered as needed, for example immediately an individual senses the onset of an episode of migraine (such as a prodrome or an aura), to pre-emptively inhibit the migraine episode, or when the individual senses a frank symptom of an episode of migraine (such as headache or other symptoms described in the subsection entitled "Migraine" of the DESCRIPTION OF THE RELATED ART) to relieve and palliate the symptoms of that episode. It is expected that the compound may be administered more than once, such as over a period of a few days, if it is first administered at the occurrence of a prodrome to continue to prevent or minimize the migraine or a symptom thereof, by scheduled administration throughout the day, such as from 2 to 6 times/day, for example from 3 to 5 times/day, such as 4 times/day. This scheduled administration may be on a uniform schedule, for example at 8 a.m., noon, 4 p.m., and 8 p.m. (for 4 times/day administration), or on a non-uniform schedule where the administration is chosen to maximize the administration at the time when the expected occurrence of migraine symptoms is most frequent or most severe, either in the migraine symptomatic population or in the individual being treated. Thus, for example, administration might be at 9 a.m., 3 p.m., 5 p.m., and 8 p.m. (again for 4 times/day) to maximize the administration at the time when the expected occurrence of symptoms is most frequent. Of course, even if scheduled administration is being used, it is possible to administer the compound on an as-needed basis if symptoms are still experienced. However, because of its rapid action, it is contemplated that there will not be a need to use it chronically: treatment can be interrupted when the individual no longer senses a migraine symptom or the risk of a migraine, and resumed when it is next needed.

Also, because of the rapid onset of effect of nasally administered 16α,17α-epoxy-10β-hydroxyestr-4-en-3-one, it is expected that the compound may be administered as an adjunct to conventional (e.g. oral or injectable) antimigraine therapy. For example, it may be used as "rescue" medication in individuals who may still suffer from an episode of a symptom of migraine even while on conventional antimigraine therapy, to relieve and palliate the symptoms of that episode as needed.

Thus nasally administered 16α,17α-epoxy-10β-hydroxyestr-4-en-3-one may be used acutely or intermittently, and alone or in combination with conventional antimigraine therapy, in the treatment of migraine.

Example 1: Electrophysiological Studies with 16α,17α-epoxy-10β-hydroxyestr-4-en-3-one 16α,17α-Epoxy-10β-hydroxyestr-4-en-3-one induced inward currents in isolated human nasal chemosensory neurons and electrotonic depolarization of the nasal septal chemosensory mucosa: the first event in chemotransduction in peripheral receptors. The amplitude of this response increased depending on the concentration of the compound, with a maximal response at $10^{-7}$ to $10^{-6}$ M. In vitro, there was no agonist or antagonist activity on estrogen, androgen, progestin and glucocorticoid receptors, nor was there any affinity for receptors of indoleamine, monoamines, ion channels, receptors, peptides, opioid, glutamate neurotransmitter, steroid hormones, or glucocorticoid receptors, suggesting that the compound exerts its effects through specific receptors that are different from the other described binding sites.

Example 2: Preclinical Studies with 16α,17α-epoxy-10β-hydroxyestr-4-en-3-one

Acute and multidose (28 day) toxicity studies in rats, mice, rabbits and dogs with single (up to 100 μg/rat, 400 μg/rabbit, 600 μg/dog) and repeated (up to 50 μg/rat/day, 300 μg/dog/day) nasal doses and single (up to 2.5 mg/kg in rats, mice, rabbits) and repeated (up to 2.5 mg/kg/day in rats and rabbits) intravenous doses of 16α,17α-epoxy-10β-hydroxyestr-4-en-3-one demonstrated that the compound was well tolerated in all species tested, with no deaths or adverse clinical signs or effects on laboratory or pathology parameters observed.

Genotoxicity tests revealed no evidence of mutagenic or clastogenic potential of the compound when examined in the Ames reverse mutation assay and the in vivo bone marrow micronucleus test. Reproductive toxicity studies in pregnant rabbits revealed no adverse effects on maternal or litter parameters attributable to the compound at intravenous doses up to 2.5 mg/kg/day administered during the period of organogenesis. Preclinical pharmacokinetic studies with the compound demonstrated very low systemic exposure when the compound was administered by repeated or singe escalating nasal doses up to 100 μg/rat, 400 μg/rabbit, 600 μg/dog. When given to rats, rabbits, or dogs in single repeated intravenous doses up to 2.5 mg/kg, plasma concentrations of the compound generally were dose-proportional and decreased rapidly.

Example 3: Preliminary Human Studies with 16α,17α-epoxy-10β-hydroxyestr-4-en-3-one (Predictive of Efficacy)

Preliminary findings showed that nasal administration of microgram quantities of 16α,17α-epoxy-10β-hydroxyestr-4-en-3-one to human volunteers of both sexes induced concentration dependent activation of the electrogram recorded from the surface of the nasal chemosensory mucosa. The half effective dose of this effect was 0.087 μg. The electrogram induced during nasal administration of 1.6 μg of 16α,17α-epoxy-10β-hydroxyestr-4-en-3-one was rapidly followed (latency 5-10 seconds) by modulation of reflex activity integrated in the limbic system, hypothalamus, and cerebral cortex. There was significantly increased amplitude of the depth of the inspiratory cycle of respiration and decreased respiration rate within physiologic range, increased amplitude of the skin conductance measured as electrodermal activity or dermo-limbic reflex from the palmar surface of the fourth and fifth finger, decreased skeletal muscle tone (relaxation) measured from the electromyogram recorded transdermally from the chin muscles, and decreased body core temperature recorded from the external ear canal. There was no significant change in cardiac rate.

The effects of 16α,17α-epoxy-10β-hydroxyestr-4-en-3-one on physiologic parameters are explained as follows:
(a) decreased respiration rate and increased depth of respiration are the result of decreased resistance of the airways induced by bronchiolar dilation. 16α,17α-Epoxy-10β-hydroxyestr-4-en-3-one decreased parasympathetic system tone resulting in increased sympathetic activity and stimulation of $\beta_2$ adrenergic receptors in the bronchiole smooth muscle that induced bronchodilation;
(b) increased skin conductance amplitude is the result of increased skin secretions, which are produced by preponderance of the sympathetic nervous system tone (or decreased parasympathetic tone);
(c) decreased body temperature is explained by increased activity of the posterior (adrenergic) hypothalamus and decreased parasympathetic tone (anterior hypothalamus). This effect was also shown in menopausal women as decreased number, severity and bother of hot flashes after nasal administration of 16α,17α-epoxy-10β-hydroxyestr-4-en-3-one; and
(d) decreased muscle tone or relaxation was induced through the efferent limbic-hypothalamic neural connections to the cortical areas.

Example 4: Human Clinical Studies with 16α,17α-epoxy-10β-hydroxyestr-4-en-3-one (Predictive of Efficacy and Safety)

In a group of 14 women of reproductive age, nasal administration of a nasal spray containing 0.5 μg of 16α,17α-epoxy-10β-hydroxyestr-4-en-3-one per administration (administration by an Aptar nasal spray pump of 50 μL of an aqueous solution of 10 μg/mL 16α,17α-epoxy-10β-hydroxyestr-4-en-3-one with 2% propylene glycol and 2% ethanol), compared to the vehicle alone, induced statistically significant decreases in respiratory frequency, skeletal muscle tone, galvanic skin reflex, and core body temperature; and a not statistically significant increase in cardiac frequency.

In another study also in women of reproductive age, nasal delivery of a nasal spray containing 1.6 μg of 16α,17α-epoxy-10β-hydroxyestr-4-en-3-one (one administration per nostril by an Aptar nasal spray pump of 50 μL of an aqueous solution of 16 μg/mL 16α,17α-epoxy-10β-hydroxyestr-4-en-3-one with 2% propylene glycol and 2% ethanol) induced a rapid (0.5 to 4 minute latency) decrease in core body temperature of 1±0.23° C. that persisted for 9±2.5 minutes. It also changed the tone of the sympathoadrenergic system (as assessed by measuring physiologic sinus arrhythmia) within 5 minutes of administration, and the effect persisted for 15 to 20 minutes.

In a randomized, double-blind, placebo-controlled test in women diagnosed with PMDD, nasal administration of 16α,17α-epoxy-10β-hydroxyestr-4-en-3-one induced significant improvements in hypothalamic (fatigue, anger, craving for foods), limbic system (mood swings, depression, lack of interest) and cortical (headache, tension) behavioral symptoms. These improvements appeared within 30 minutes after single dose nasal administration of the formulation and persisted for approximately 5 hours. Because of the excellent safety profile of 16α,17α-epoxy-10β-hydroxyestr-4-en-3-one and lack of systemic exposure demonstrated in a pharmacokinetic bioavailability study, the medication was repeated up to 6 times daily. No serious adverse events were reported, and the side effects were minimal and similar to administration of placebo.

Therefore, nasal administration of 16α,17α-epoxy-10β-hydroxyestr-4-en-3-one starting at the onset of behavioral symptoms of PMDD (similar to migraine prodromes) activates neural circuits in the limbic-hypothalamic areas of the brain that improves behavioral functioning (mood swings, anger, tension, stress). This prevents the increase in tone of the parasympathetic system and the release of vasoactive and nociceptive molecules from the meningeal vessels, resulting in deactivation of the trigeminovascular pathway.

These effects, including especially decreased skeletal muscle tension, decreased galvanic skin reflex frequency of events, and decrease in fatigue, headache, tension, depression, irritability/anger, anhedonia, and food cravings, are predictive of the efficacy and safety of the nasal administration of 16α,17α-epoxy-10β-hydroxyestr-4-en-3-one in the treatment of migraine.

Example 5: Human Clinical Studies with 16α,17α-epoxy-10β-hydroxyestr-4-en-3-one in Migraine Patients (Demonstrative of Efficacy and Safety)

In an exploratory single-blind study, one control subject and two subjects with chronic migraine (diagnosed according to the *International Classification of Headache Disorders*, $3^{rd}$ edition) with a history of regular migraine attacks lasting typically one to three days, participated in two identical study sessions separated by one week, with the migraine subjects instructed to participate during the first day of a migraine attack. Each subject was given a baseline evaluation using the Hamilton Anxiety Scale (HAM-A), a clinician-administered rating scale developed to quantify the severity of anxiety symptomatology, and the Hamilton Depression Rating Scale (HAM-D), a clinician-administered rating scale developer to quantify severity of depression; and was asked to assess their migraine pain using a 6-point visual reference scale (VRS), with 0=no pain, 1=mild pain, 2=moderate pain, 3=severe pain, 4=very severe, 5=most severe pain imaginable. Each subject was then treated with a single nasal administration of a placebo formulation during the first study session, and with a single nasal administration of 6.4 μg of 16α,17α-epoxy-10β-hydroxyestr-4-en-3-one during the second study session. After 15 minutes, each subject was asked to reassess their pain level, and given a resting state fMRI scan. They were then re-evaluated on the HAM-A and HAM-D scales. The study intends to accumulate a total of 30 subjects.

The control subject was a 35 year old woman free from migraine, anxiety, and depression; the two migraine subjects were a 38 year old woman (with a history of 14 years of migraine, 19 days/month of headache of which 9 days/month were severe, migraine with aura, anxiety, and depression) and a 41 year old man (with a history of 5 years of migraine, 13 days/month of headache of which 4 days/month were severe, and depression).

All three subjects tolerated nasal 16α,17α-epoxy-10β-hydroxyestr-4-en-3-one and there were no reports of side effects or adverse effects. Although both migraine subjects showed mild anxiety and depression at admission, nasal 16α,17α-epoxy-10β-hydroxyestr-4-en-3-one significantly improved anxiety scores (p<0.01), and there was an improvement trend in depression scores in both subjects but this did not reach statistical significance. Nasal 16α,17α-epoxy-10β-hydroxyestr-4-en-3-one produced significant improvement in headache pain intensity scores in the migraine subjects assessed using the VRS, with a mean decrease of 2.5 relative to placebo (p<0.01). The migraine patients showed improvement in functional connectivity of the brain areas studied: relative to placebo, nasal 16α,17α-epoxy-10β-hydroxyestr-4-en-3-one decreased functional connectivity of the hypothalamus with the anterior orbital gyrus, the right medial orbital gyms and the pons, increased functional connectivity of the amygdala with the anterior occipital lobe and the right middle occipital lobe, decreased functional connectivity of the right thalamus with the left orbitofrontal cortex, superior parietal lobe, left insular cortex and left primary motor cortex, and increased functional connectivity with the left somatosensory cortex; representing a trend towards the values of the healthy control.

These effects, including especially the decrease in pain, anxiety, and depression, on nasal administration of 16α,17α-epoxy-10β-hydroxyestr-4-en-3-one demonstrate the efficacy and safety of the nasal administration of 16α,17α-epoxy-10β-hydroxyestr-4-en-3-one in the treatment of migraine.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

What is claimed is:

1. A method of treating migraine in an individual suffering therefrom, comprising nasal administration of a therapeutically effective amount of 16α,17α-epoxy-10β-hydroxyestr-4-en-3-one, where the therapeutically effective amount is the amount of 16α,17α-epoxy-10β-hydroxyestr-4-en-3-one that, when administered to the nasal chemosensory receptors of an individual suffering from migraine, is sufficient to effect treatment for the migraine, but which amount is insufficient to have a systemic effect on the migraine by absorption into the circulation.

2. The method of claim 1, where the nasal administration includes vomeronasal administration.

3. The method of claim 1, where the individual is a man.

4. The method of claim 1, where the individual is a woman.

5. The method of claim 1, where the 16α,17α-epoxy-10β-hydroxyestr-4-en-3-one is administered at the onset of a migraine symptom.

6. The method of claim 1, where the 16α,17α-epoxy-10β-hydroxyestr-4-en-3-one is administered at the onset of a migraine prodrome or aura.

7. The method of claim 6, where the 16α,17α-epoxy-10β-hydroxyestr-4-en-3-one is administered at the onset of a migraine prodrome.

8. The method of claim 6, where the 16α,17α-epoxy-10β-hydroxyestr-4-en-3-one is administered at the onset of an aura.

9. The method of claim 1, where the 16α,17α-epoxy-10β-hydroxyestr-4-en-3-one is administered on a schedule throughout the day.

10. The method of claim 9 where the 16α,17α-epoxy-10β-hydroxyestr-4-en-3-one is administered from 2 to 6 times per day.

11. The method of claim 10, where the 16α,17α-epoxy-10β-hydroxyestr-4-en-3-one is administered from 3 to 5 times per day.

12. The method of claim 11, where the 16α,17α-epoxy-10β-hydroxyestr-4-en-3-one is administered 4 times per day.

13. The method of claim 9, where the administration of the 16α,17α-epoxy-10β-hydroxyestr-4-en-3-one is chosen to maximize the administration at the time when the expected occurrence of migraine symptoms is most frequent or most severe in the migraine symptomatic population, or in the individual being treated.

14. The method of claim 1, where the 16α,17α-epoxy-10β-hydroxyestr-4-en-3-one is administered in a pharmaceutical formulation.

15. The method of claim 14, where the pharmaceutical formulation is a nasal spray.

16. The method of claim 15, where the nasal spray comprises an aqueous solution of 16α,17α-epoxy-10β-hydroxyestr-4-en-3-one.

17. The method of claim 16, where the 16α,17α-epoxy-10β-hydroxyestr-4-en-3-one content of the nasal spray is 0.8 μg to 19.2 μg per administration.

18. The method of claim 17, where the 16α,17α-epoxy-10β-hydroxyestr-4-en-3-one content of the nasal spray is 1.6 μg to 9.6 μg per administration.

19. The method of claim 18, where the 16α,17α-epoxy-10β-hydroxyestr-4-en-3-one content of the nasal spray is 1.6 μg, 3.2 μg, or 6.4 μg per administration.

20. The method of claim 1, where the migraine is associated with previous traumatic brain injury.

* * * * *